United States Patent [19]
Loos

[11] Patent Number: 6,081,744
[45] Date of Patent: *Jun. 27, 2000

[54] ELECTRIC FRINGE FIELD GENERATOR FOR MANIPULATING NERVOUS SYSTEMS

[76] Inventor: Hendricus G. Loos, 3019 Cresta Way, Laguna Beach, Calif. 92651

[*] Notice: This patent is subject to a terminal disclaimer.

[21] Appl. No.: 09/118,505

[22] Filed: Jul. 17, 1998

Related U.S. Application Data

[63] Continuation-in-part of application No. 08/788,582, Jan. 24, 1997, Pat. No. 5,782,874, which is a continuation-in-part of application No. 08/447,394, May 23, 1995, abandoned, which is a continuation of application No. 08/068,748, May 28, 1993, abandoned.

[51] Int. Cl.$^7$ ........................................... A61N 1/36
[52] U.S. Cl. ............................................. 607/2
[58] Field of Search ...................................... 607/2

[56] References Cited

U.S. PATENT DOCUMENTS

| | | | |
|---|---|---|---|
| 1,973,911 | 9/1934 | Ruben | 607/152 |
| 3,678,337 | 7/1972 | Grauvogel | 128/419 N |
| 3,840,020 | 10/1974 | Smith | 128/419 N |
| 3,886,932 | 6/1975 | Suessmilch | 128/908 |
| 3,941,136 | 3/1976 | Bucalo | 607/39 |
| 4,084,595 | 4/1978 | Miller | 128/422 |
| 4,197,851 | 4/1980 | Fellus | 128/422 |
| 4,292,980 | 10/1981 | Suzuki | 128/419 N |
| 4,611,599 | 9/1986 | Bentall et al. | 178/422 |
| 4,856,526 | 8/1989 | Liss et al. | 128/422 |
| 5,169,380 | 12/1992 | Brennan | 600/26 |

FOREIGN PATENT DOCUMENTS

| | | | |
|---|---|---|---|
| 0285415 | 12/1965 | Australia | 607/2 |
| 3327126 | 4/1984 | Germany | 607/2 |
| 2164563 | 3/1986 | United Kingdom | 607/2 |

OTHER PUBLICATIONS

N. Wiener, Nonlinear Problems in Random Theory, 1958, p. 72, 72.

M. Hutchinson, Megabrain, 1991, p. 233–245.

*Primary Examiner*—William E. Kamm

[57] ABSTRACT

Apparatus and method for manipulating the nervous system of a subject through afferent nerves, modulated by externally applied weak fluctuating electric fields, tuned to certain frequencies such as to excite a resonance in neural circuits. Depending on the frequency chosen, excitation of such resonances causes in a human subject relaxation, sleepiness, sexual excitement, or the slowing of certain cortical processes. The electric field used for stimulation of the subject is induced by a pair of field electrodes charged to opposite polarity and placed such that the subject is entirely outside the space between the field electrodes. Such configuration allows for very compact devices where the field electrodes and a battery-powered voltage generator are contained in a small casing, such as a powder box. The stimulation by the weak external electric field relies on frequency modulation of spontaneous spiking patterns of afferent nerves. The method and apparatus can be used by the general public as an aid to relaxation, sleep, or arousal, and clinically for the control and perhaps the treatment of tremors and seizures, and disorders of the autonomic nervous system, such as panic attacks.

9 Claims, 5 Drawing Sheets

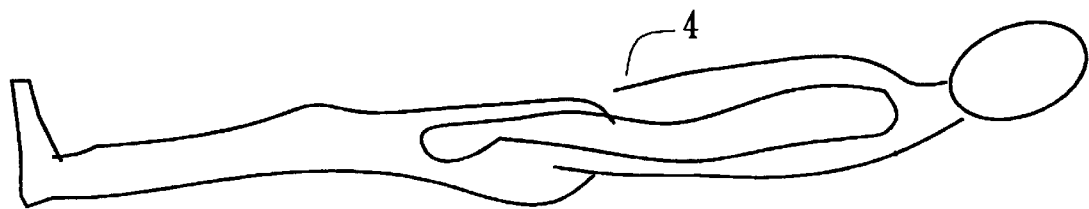
FIG. 7
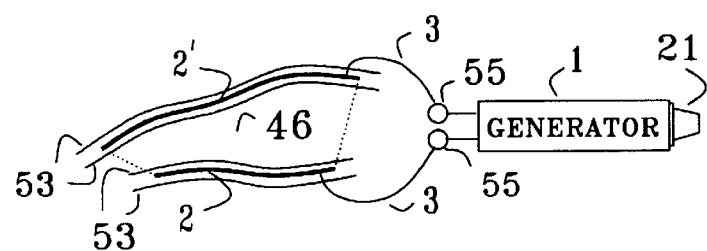
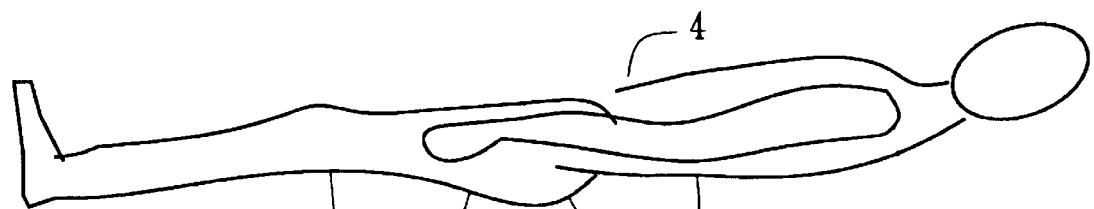
FIG. 8
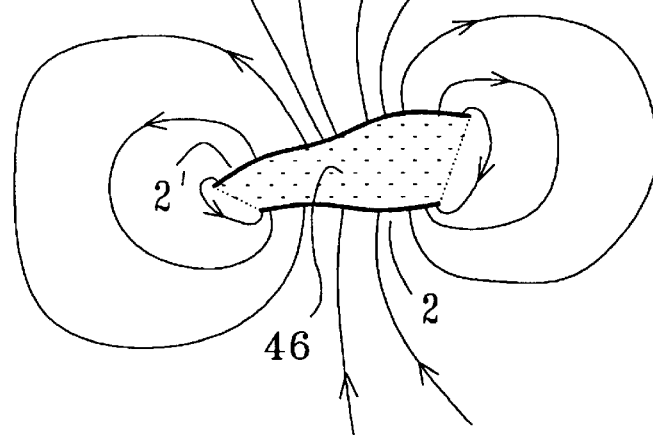

ELECTRIC FRINGE FIELD GENERATOR FOR MANIPULATING NERVOUS SYSTEMS

Continuation in part of Ser. No. 08/788,582, Jan 24, 1997, U.S. Pat. No. 5,782,874, which is a continuation in part of Ser. No. 08/447,394, May 23, 1995, abandoned, which is a continuation of Ser. No. 08/068,748, May 28, 1993, abandoned.

BACKGROUND OF THE INVENTION

The invention relates to neurostimulation of a subject by an external electric field, induced by field electrodes positioned away from the subject. Fluctuations of the field induce electric currents in the subject's body, since bulk biological tissue is a rather good conductor of electricity.

A neurological effect of external electric fields has been mentioned by Norbert Wiener, in discussing the bunching of brain waves through nonlinear interactions. The electric field was arranged to provide "a direct driving of the brain". Wiener describes the field as set up by a 10 Hz alternating voltage of 400 V applied in a room between ceiling and ground.

In U.S. Pat. No. 5,169,380 Brennan describes an apparatus for alleviating disruptions in the circadian rythms of a mammal, where an alternating electric field is applied across the head. The voltage applied to the electrodes is specified as at least 100 V, and the peak-to-peak value of the field as at least 590 V/m in free air before deploying the electrodes across the head of the subject. The alternating electric field has a frequency in the range from 5 to 40 Hz. Brennan states that the method is aimed at subjecting at least part of the subject's brain to an alternating electric field, in the belief that this would stimulate the influx of calcium ions into nerve endings, which in turn would "regulate and facilitate the release of neurotransmitters". It should be noted that electric polarization of the head causes the field strength in the narrow space between electrode and skin to be about a factor $h/2d$ larger than the free-air strength, h being the distance between the electrodes and d the spacing between electrode and skin. For h=17 cm and d=5 mm the factor comes to 17, so that with the specified free-air field of at least 590 V/m the field in the gap between electrode and skin is at least 10 KV/m peak to peak.

A device that involves a field electrode as well as a contact electrode is the "Graham Potentializer" mentioned by Hutchison. This relaxation device uses motion, light, and sound as well as an external alternating electric field, applied mainly to the head. The contact electrode is a metal bar in physical contact with the bare feet of the subject; the field electrode has the form of a hemispherical metal headpiece several inches from the subject's head. According to the brief description by Hutchison, a signal of less than 3 Volts at a frequency of 125 Hz is applied between the field electrode and the contact electrode. In this configuration, the contact electrode supplies to the body the current for charging the capacitor formed by the headpiece field electrode and the apposing area of skin. The resulting electric field stands mainly between the head piece and the scalp. In the three external field arrangements mentioned, viz., Wiener, Brennan, and Graham, the electric field is applied to the head, thereby subjecting the brain to polarization currents. These currents run through the brain in a broad swath, with a distribution determined by the bulk geometry and nonuniformities of conductivity and permittivity. The scale of the current density is conveniently taken as its maximum value on the skin of the head. For sinusoidal fields this scale is easily calculated as the product of radian frequency, vacuum permittivity, and maximum amplitude of the external field on the head. Using Brennan's lowest frequency of 5 Hz, his minimum free-air field strength of 590 V/m, and the factor 17 as estimated above to account for polarization of the head by the applied field, the scale of the polarization current density in the brain comes to about 280 $pA/cm^2$. In the absence of an understanding of the neurological effects involved, it is prudent to avoid exposing the brain to artificial bulk currents of such scale, and apply a factor $1/4000$ for safety. Accordingly, polarization current densities in the brain in excess of 70 $pA/cm^2$ are considered substantial.

It is an object of the present invention to obtain a method and apparatus for manipulating the nervous system by means of external electric fields without causing substantial polarization currents in the brain.

The use of electric fields raises concerns about possible health effects. Such concerns have been widely discussed in the news media in regard to electric power lines and electric apparatus. Answering the pertinent questions by objective research will take time, but meanwhile governments have been setting guidelines for safe limits on field strengths. At present, the strictest conditions of this sort are the Swedish MPRII guidelines. Magnetic fields are of no concern here, because the currents involved are so small. But the electric field must be considered, since even at low voltages strong electric fields can result from field electrodes placed close to the skin. With respect to extremely low frequency electric fields, the MPRII guidelines limit the field strength to 25 V/m in the frequency range from 5 Hz to 2 KHz. In the Brennan patent the minimum field strength of 590 V/m violates the guidelines by a factor 24; when polarization effects are accounted for, the factor is about 400. It is a further object of the present invention to manipulate the nervous system by using external electric fields that are in compliance with the MPRII guidelines.

Brennan stipulates voltages of at least 100 V, and as high as 600 V for the preferred embodiment. Generation of such voltages requires a voltage multiplication stage, if low voltage battery operation is desired. This increases the current drain and the size of the generator. The large voltages also raise safety concerns. It is yet a further object of the present invention to manipulate the nervous system by means of external electric fields, using low voltages that are generated by small and safe battery-operated devices with low current consumption.

In the arrangements of Wiener and Brennan, the electric field is induced by field electrodes that are positioned at opposite sides of the subject. This limits portability and convenience of use. It is a further object of the present invention to provide a method and apparatus for the manipulation of the the nervous system by electric fields in a manner which does not require field electrodes placed at opposite sides of the subject's body.

SUMMARY

Experiments have shown that weak electric fields of frequency near ½ Hz applied externally to the skin of a human subject can cause relaxation, doziness, ptosis of the eyelids, or sexual excitement, depending on the precise frequency used. In these experiments, the electric field was applied predominantly to skin areas away from the head. Apparently, the external electric field somehow influences somatosensory or visceral afferent nerves, which report the effect to the brain. Although the mechanism whereby the field acts on the afferents or their receptors is unknown, the effect must take the form of a slight modulation of spontaneous spiking patterns of nerves, because the polarization current densities induced by the field are much too small to cause firing of the nerve. If the applied field is periodic, so will be the modulation of the spiking patterns, and the brain is then exposed to an evoked periodic signal input. Apparently, this signal input excites certain resonant neural circuits, the state of which has observable consequences. Since the resonances are excited through somatosensory or visceral afferents, they are called "sensory resonances".

Besides the resonance near ½ Hz that affects the autonomic nervous system, we have also found a resonance near 2.4 Hz which slows certain cortical processes. For both resonances the electric field strength on the skin must lie in a certain limited range for the physiological effects to occur. This "effective intensity window" can be determined accurately for the 2.4 Hz resonance, by measuring the time needed to count silently backward from 100 to 60.

The external electric field used for stimulation is induced by a pair of field electrodes placed such that the subject is entirely outside the space between the field electrodes, thereby affording compact field electrode configurations and convenience of deployment. In fact, a pair of field electrodes can be contained together with the voltage generator in a single small casing, such as a powder box. Such a small device can be used conveniently by the general public as an aid to relaxation, sleep, or sexual excitement, and clinically for the control and perhaps a treatment of tremors and seizures, and disorders of the autonomic nervous system such as panic attacks.

Two or more pairs of field electrodes may be combined to advantage if the field outside the space between the electrodes is used as stimulant. Two pairs deployed close to the skin can be balanced such that the resulting field stands essentially only on the skin area directly apposed to field electrodes, the field over the rest of the body being negligible. In another configuration, m pairs of field electrodes can be combined in an assembly which features so called full compensation, where in the multipole expansion of the induced potential at large distances the contributions of the individual pairs to the first m−1 terms cancel each other. The electric field of the assembly is then asymptotically multipole of order 2m, so that the field falls off as the inverse 2m+1 th power of distance, thus featuring a short range and directional properties.

Such a multipole electrode with a fully compensated assembly of 4 field electrode pairs, driven by a small low-voltage generator powered by a standard 9 V battery, has been used effectively as a sleeping aid. The thin multipole electrode was placed under a mattress about 13 cm below the subject, such that the main emission lobe was roughly at lumbar height. With the same setup, a man can arrange for rather intense and prolonged sexual excitiment by assuming a position on the mattress such that the main emission lobe from the multipole electrode intersects his perinaeum.

DESCRIPTION OF THE DRAWINGS

FIG. 7 shows a pair of field electrodes charged to opposite polarity, and positioned such that the subject is entirely outside the space between the field electrodes.

FIG. 8 illustrates the electric field of the electrode pair of FIG. 7 in the presence of a subject that is entirely outside the space between the electrodes.

DETAILED DESCRIPTION

Figure 1:
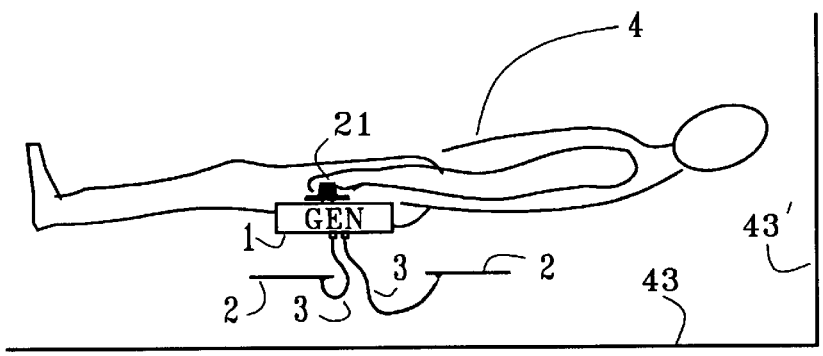
FIG. 1 depicts a preferred embodiment, showing the placement of field electrodes on one side of the subject's body.

The invention is based on the discovery, made in our laboratory, that neurological effects can be induced in a human subject by weak external low frequency electric fields, applied to skin areas away from the head. For example, application of rounded square wave fields with a peak amplitude of about 1 V/m and a frequency near ½ Hz to lower-body skin areas induces ptosis of the eyelids, relaxation, drowziness, a pressure sensation at a spot about 1 cm above the bridge of the nose, seeing moving patterns of dark purple and greenish yellow with the eyes closed, a tonic smile, a tense feeling in the stomach, sudden loose stool, and sexual excitement, depending on the precise frequency used.

The sharp frequency dependence of the observed physiological effects suggests that one is dealing here with a resonance phenomenon which involves resonant states of neural circuits.

The mentioned physiological effects were observed initially for external field strengths in the range from 1 to 25 V/m, but recent experiments have shown effects with much weaker and stronger fields.

In classical electrical nerve stimulation one applies currents of a magnitude and duration large enough to cause firing of nerves, as expressed by the so called strength-duration curve with typical times of 0.1 ms and currents of the order of 1 mA.

In our experiments the electric currents induced in the subject's body by the external electric field are orders of magnitude too small for causing classical nerve stimulation. Yet, the experiments show that a localized external field applied to skin areas away from the head elicits effects that are reported to the brain by afferent nerves; the possibility that high-conductivity pathways such as blood, lymph, or spinal fluid play an essential role in the process has been ruled out by dedicated experiments. Since classical nerve stimulation does not occur in the experiments, the afferent signals must have the form of a modulation of spontaneous spiking patterns. The simplest such modulation is frequency modulation (fm), but more subtle modulation modes [10] may be involved. For simplicity of description however, we will refer to the modulation as fm. In our experiments the modulation is very shallow, but evidently the weak incoming fm signals can cause excitation of a resonance in certain receptive neural circuits. In order to be susceptible to modulation by the weak external electric fields, sensory and visceral receptors and afferents must exhibit spontaneous spiking.

Judging by the physiological effects mentioned, the sensory resonance near ½ Hz involves the autonomic nervous system and it is therefore sometimes called the ½ Hz autonomic resonance. Another sensory resonance has been found near 2.4 Hz; it shows up as a considerable increase in the time of silently counting backward from 100 to 60, as fast as possible, with the eyes closed. The counting is done with the "silent voice" which involves motor activation of the larynx appropriate to the numbers to be uttered, but without the passage of air, or movement of mouth muscles. Since counting is a cortical process, the 2.4 Hz resonance may be called a cortical sensory resonance. In addition to affecting the silent counting, the 2.4 Hz resonance is expected to influence some other cortical processes as well. It was found that in the long run the resonance has a sleep inducing effect. Very long exposures have caused dizziness. Using another excitation modality, a new cortical resonance has been spotted near 10 Hz; this resonance speeds up rather than slows the silent counting.

Exploitation of sensory resonances and reliance on modulation of spontaneous spiking patterns of afferent nerves makes it possible to manipulate nervous systems with small fields, produced by low voltages. Moreover, employing the natural signal pathways of afferent nerves into the brain allows application of the field to skin areas away from the head. The invention thereby meets the stated objects of providing manipulation of the nervous system without causing substantial polarization current densities in the brain, compliance with the MPRII field limits, and use of low voltage battery-operated generators with small current consumption.

The invention provides a method and appartus for manipulating the nervous system of subjects. Such manipulation includes relaxation and the induction of sleep or arousal, as well as the control and perhaps a treatment of tremors, seizures, and disorders resulting from malfunctions of the autonomic nervous sytem, such as panic attacks.

The equipment suitable for the generation of the weak electric fields used for the modulation of afferent nerves consists of field electrodes and a voltage generator. The field electrodes can simply be conductive foils, wires, or meshes that may be covered with an insulating layer. The field electrodes are to be electrically connected to the generator, but insulated from the subject. The voltage generator is to produce a low fluctuating voltage. The fluctuation may be sinusoidal, square wave with various values of duty cycle, rounded or not, triangular, trapezoidal, or a combination of these shapes at the same or different frequencies; it need not even to be periodic, but may have a complicated spectrum, as long as there is sufficient energy at or near the resonance frequency of the sensory resonance of interest. For a human subject the sensory resonance frequencies known at present lie in the range from 0.1 to 45 Hz. Automatic control of the fluctuating voltage can be provided in the form of an automatic frequency shift or automatic shutoff, after elapse of a certain time interval, or more elaborate arrangements such as frequency and on/off schedules.

A preferred embodiment of the invention is shown in FIG. 1, where the voltage generator 1, labelled as "GEN", is connected to the field electrodes 2 by wires 3; the field electrodes 2 are positioned away from and on one side of the subject 4. The voltage generator may be tuned manually with the tuning control 21. As an option, sheet conductors 43 and 43', such as aluminum foils may be placed near the subject in order to diminish interference from a 60 Hz or 50 Hz house field, to be discussed.

Figure 2:
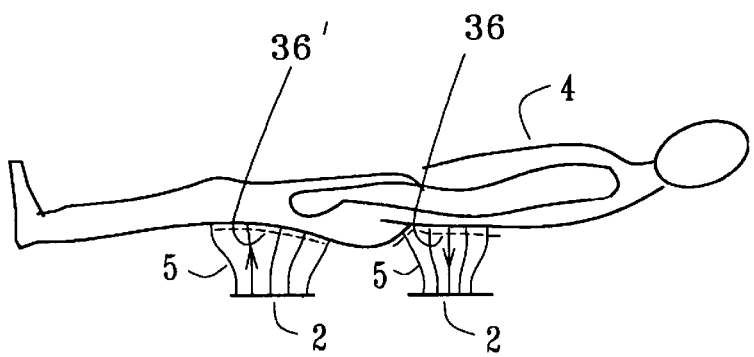
FIG. 2 illustrates the electric field generated between the field electrodes and the subject's body.

In the present invention the external electric field is applied predominantly to certain selected areas of the skin of the subject, such as areas 36 and 36' in FIG. 2, which also shows field lines 5 incident on the subject 4. The skin area of predominant field application is here defined as the set of points on the skin at which the absolute value of the resultant field strength is at least twice the average over the skin. The resultant field includes the electric field produced by polarization charges on the skin. To avoid induction of substantial polarization current densities in the brain, the skin area of predominant field application should be chosen away, i.e., at least 10 cm, from the head.

Figure 3:
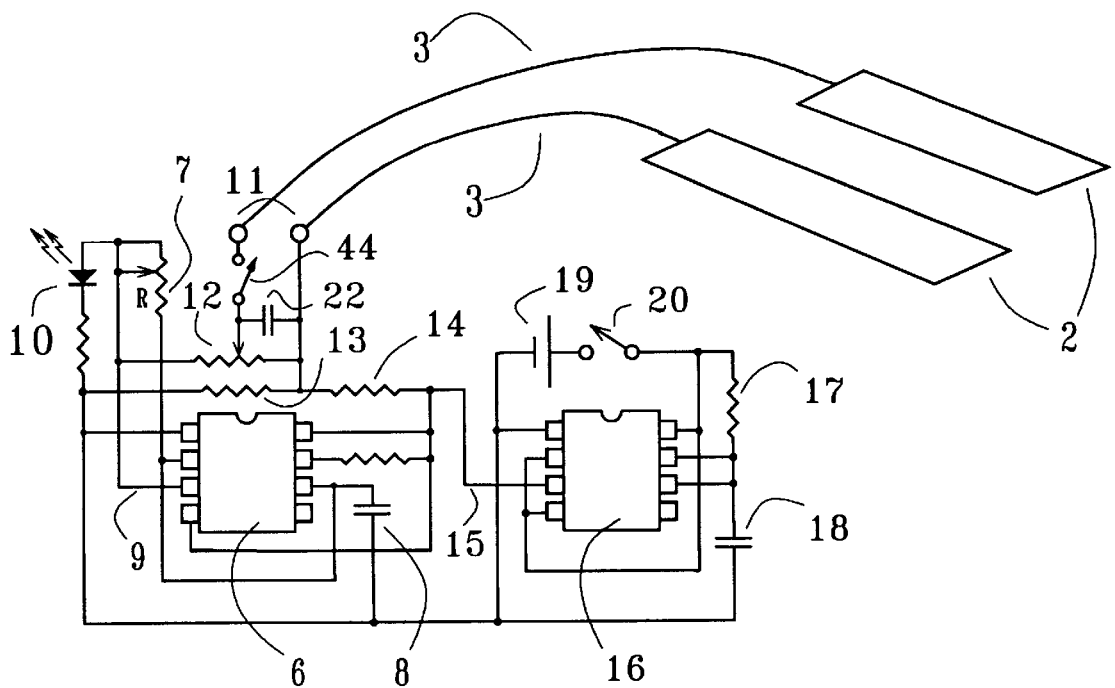
FIG. 3 shows a generator for an electric field that fluctuates as a rounded square wave, and has an automatic shutoff.
Figure 12:
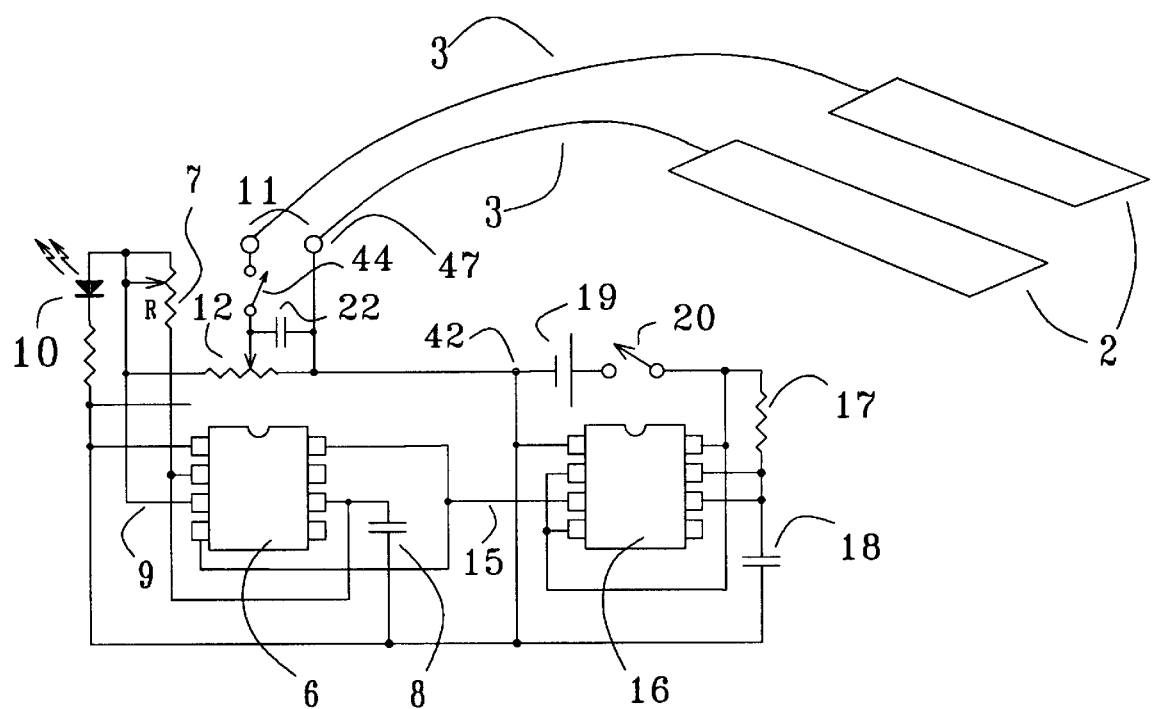
FIG. 12 shows a circuit for generating a single-polarity pulse.

A suitable voltage generator, built around two RC timers, is shown in FIG. 3. Timer 6 (Intersil ICM7555) is hooked up for astable operation; it produces a square wave voltage with a frequency determined by resistor 7 and capacitor 8. The square wave voltage at output 9 drives the LED 10, and appears at one of the output terminals 11, after voltage division by potentiometer 12. The other output terminal is connected to an intermediate voltage produced by the resistors 13 and 14. As a result, the voltage between the output terminals 11 alternates between positive and negative values. Automatic shutoff of the voltage that powers the timer, at point 15, is provided by a second timer 16 (Intersil ICM7555), hooked up for monostable operation. The shutoff occurs after a time interval determined by resistor 17 and capacitor 18. Timer 16 is powered by a 3 V battery 19, controlled by the switch 20. The output terminals 11 are connected to the field electrodes 2 by conductors 3. The resistors 13 and 14 not only serve as a voltage divider that gives the intermediate voltage to produce an alternating square wave, but provide current limitation as well. A further decrease of the currents induced in the subject is caused by the output capacitor 22. There is the option of including a switch 44 in the output circuit, in order to prevent polarization of the electrode assembly by a 60 or 50 Hz house field when the device is inactive. The circuit shown produces an alternating square wave at the output terminals 11. Instead, a single polarity wave may be used, which amounts to adding a constant bias field. By itself, such a field does not give rise to polarization currents, so that the physiological effect is the same as for an alternating field, as long as the subject is not moving. A single-polarity wave may be obtained, as shown in FIG. 12, by connecting the negative battery terminal 42 to the output terminal 47.

Figure 4:
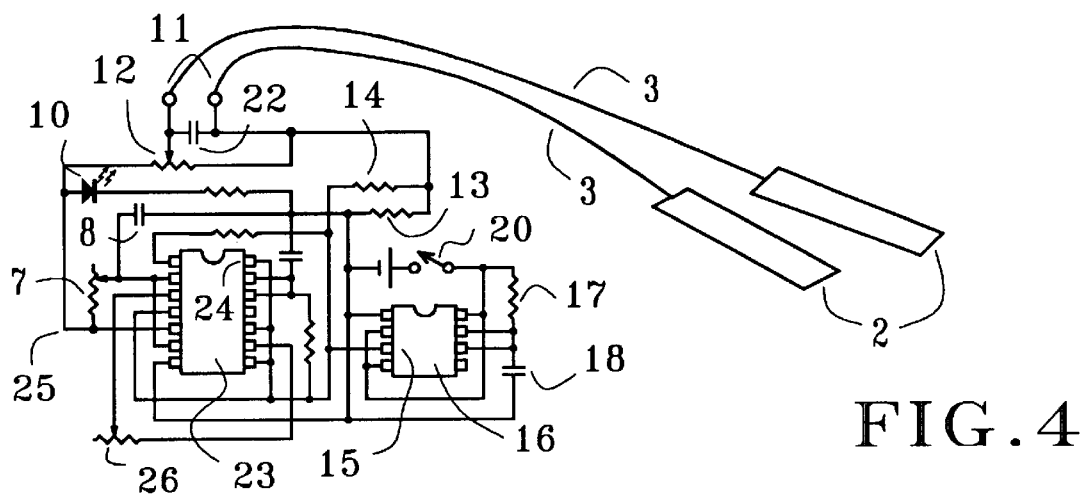
FIG. 4 shows a generator for an electric field that fluctuates as a rounded square wave, and has an automatic frequency shift and shutoff.

A time variation of frequency may be accomplished by manipulating the control voltage section of a dual timer with theoutput of the other section. An embodiment for this type of operation is shown in FIG. 4. The dual timer 23 (Intersil ICM7556) is powered at point 24 by voltage from the output 15 of timer 16 (Intersil ICM7555), which serves as an automatic shutoff after a time interval determined by resistor 17 and capacitor 18. The timer operation is started by closing the switch 20. The voltage at output 25 of the dual timer 23 drives the LED 10, and is applied, via the variable resistor 12, to one of the terminals of output 11 of the voltage generator. Resistors 14 and 13 provide an intermediate voltage at the other terminal of the output 11, such as to result in a potential difference between the output terminals that alternates between positive and negative values of substantially equal magnitudes. The frequency of the square wave at point 25 depends on resistor 7 and capacitor 8. The frequency is also influenced by the control voltage applied to the timer. A frequency upshift can be obtained by applying the output of the second section of the dual timer 23 to the control voltage pin of the first timer section, via resistor 26. This second timer section is hooked up for monostable operation. The output terminals 11 are connected by conductors 3 to the field electrodes 2, which are pieces of aluminum foil, covered by insulating tape on both sides. Low frequencies can be monitored with an LED 10 of FIG. 3. The LED blinks on and off with the square wave, and it doubles as a power indicator. The frequency can be determined by reading a clock and counting LED light pulses. For higher frequencies a monitoring LED can still be used, if it is driven by a wave obtained by frequency division of the generator output wave.

Figure 13:
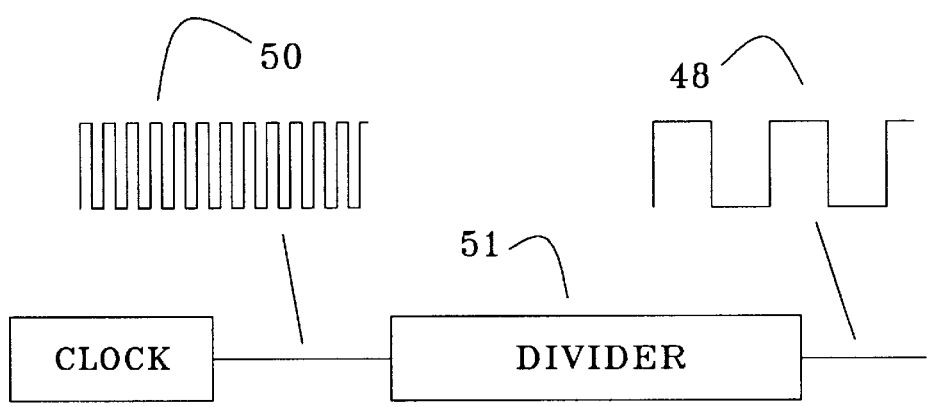
FIG. 13 shows how to obtain a square wave from a clock signal by frequency division.

The voltage generators discussed above have oscillators of the RC type, but other types of low voltage oscillators can be used as well. For instance, the voltage generator can be built as a digital device, shown in FIG. 13, in which a square wave output 48 is derived from a clock signal 50 by a frequency divider 51. Chaotic signals, time variation of frequency, programmed frequency sequences, automatic turn on and shutdown, frequency adjustment, and frequency monitoring may also be accomplished digitally. A computer that runs a simple timing program can be used for the generation of all sorts of square waves that can be made available at a computer port. A economic and compact version of such an arrangement is provided by the Basic Stamp, which has an onboard EEPROM that can be programmed for the automatic control of the fluctuating voltage generated, such as to provide desired on/off times, frequency schedules, or chaotic waves. In the interest of controlling polarization current peaks or complying with MPRII guidelines, the square waves can be rounded by RC circuits, and further smoothed by integration and filtering. In this manner, a near-sinusoidal output can be achieved. Such output can also be obtained with a digital sine wave generator based on a walking ring counter, or with a waveform generator chip such as the Intersil ICL8038. Analog circuits for tunable sine wave generators based on LC oscillators with passive inductance and capacitance are not practical for the present purpose because of the very large component parameter values required at the low frequencies. Large inductances can be produced by a compact active stage, or one can use two separate RC phase shift circuits connected in a loop with an amplitude limiter. Tuning may be done with a single potentiometer.

Applications are envisioned in which the field electrodes are driven by a fluctuating voltage that is chaotic. Such a voltage is here defined as having pseudo-random mean crossing times, or peak times, or both. A simple example is provided by a a square wave for which the transition time intervals form a pseudo-random sequence, within rather close upper and lower limits. The brain is adaptive, but the chaotic transitions are difficult to learn and anticipate, and therefore a field with a slightly chaotic square wave may thwart habituation. A sensory resonance can still be excited by such a wave, if it has a pronounced spectral peak close to the resonant frequency. The chaotic wave can also be used for upsetting pathological oscillatory modes in neutral circuits, thereby providing some measure of control of tremors, for instance in Parkinson patients.

Figure 5:
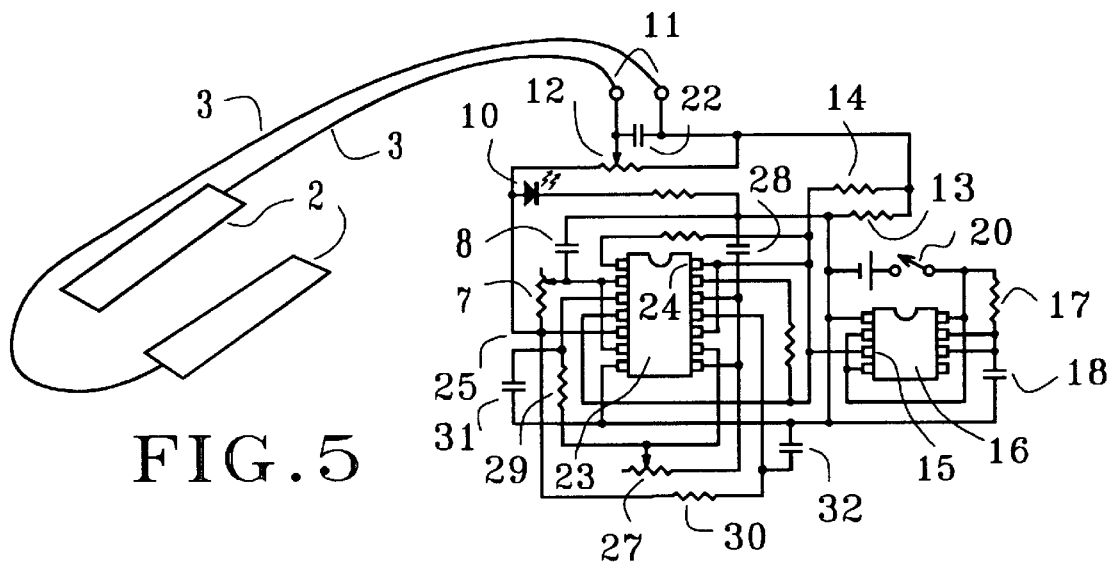
FIG. 5 shows a generator for an electric field that fluctuates as a rounded square wave with a chaotic time dependence, and has an automatic shutoff.

An embodiment which involves a chaotic square wave electric field is shown in FIG. 5. The dual timer 23 (Intersil ICM7555) is powered, at point 24, by the output 15 of timer 16 (Intersil ICM7555), hooked up for monostable operation, such as to provide automatic shutoff after a time determined by resistor 17 and capacitor 18. Operation of timer 16 is started by closing switch 20. Both sections of the dual timer 23 are hooked up for bistable operation, with slightly different RC times. The voltage at output 25 of the first timer section is used to drive the LED 10; after voltage division by the variable resistor 12, the voltage is applied to one of outputs 11. The other output 11 is an intermediate voltage from the voltage divider formed by resistors 14 and 13. The outputs 11 are connected to the field electrodes 2 through conductors 3. The RC time of the first timer section is determined by resistor 7 and capacitor 8. The RC time of the second timer section is determined by resistor 27 and capacitor 28. The two timer sections are coupled by connecting their outputs crosswise to the control voltage points, via resistors 29 and 30. with capacitors 31 and 32 to ground. For a proper range of component values, the square wave output of each of the timer sections is chaotic. An example, the following component values result in a satisfactory chaotic output: $R_7$=1.22 M$\Omega$, $R_{27}$=1.10 M$\Omega$, $R_{29}$=440 K$\Omega$), $R_{30}$=700 K$\Omega$, $C_8$=0.68 $\mu$f, $C_{28}$=1.0 $\mu$f, $C_{31}$=4.7 $\mu$f, and $C_{32}$=4.7 $\mu$f. Tests with a subject who is not a Parkinson patient, but who has a hand tremor of another origin, have shown good control of the tremor by a square wave chaotic electric field with chaotic time dependence, using the generator of FIG. 5 with the component values given above, and with electrodes placed vertically on two opposite vertical sides of the seat cushion of an easy chair.

Figure 6:
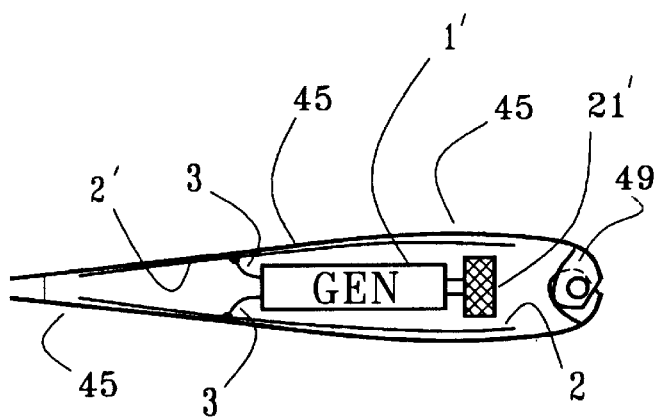
FIG. 6 shows an embodiment with the field electrodes and generator contained in a single casing.

Of convenience in social settings is an embodiment in which a pair of field electrodes and a voltage generator are contained in a single casing such as a small box, purse, powder box, or wallet. An embodiment of this type is shown in FIG. 6, where the generator 1' with tuning control 21' is placed inside a powder box casing 45 with hinge 49. The field electrodes 2 and 2' are contained in the casing 45. The field electrodes 2 are connected to the generator 1' by conductors 3. For brevity, field electrodes mounted on the outside surface of the casing are considered as contained in the casing.

The peak-to-peak variation of the output voltage of the voltage generators discussed above cannot exceed 16 V, because of supply voltage limitations for the CMOS timer chips. However, much lower output voltages suffice for most applications. An output voltage of 2.4 volts peak to peak is adequate for the setup of FIG. 1. Such an output voltage is provided by the signal generators of FIGS. 3 and 4, when powered by a 3 V battery. The small voltages suffice even for embodiments in which the generator and the field electrodes are mounted in a single small box, in spite of the small area available for the electrodes.

In applications of modulation of afferent nerves by an external electric field there is usually also present a 60 Hz or 50 Hz house field, i.e., an electric field emanating from house wiring, electric apparatus and electric power lines. House fields can have considerable strength; Becker and Marino list the electric field, at 1 ft distance from an electric blanket, broiler, refrigerator, food mixer, hairdryer, color TV, and light bulb respectively as 250, 130, 60, 50, 40, 30, and 2 V/m. The house field may cause inadvertent modulation of afferent nerves that interferes with the purposeful modulation of the present invention. Such interference may be diminished by decreasing the strength of the house field incident on the subject, by placing near the subject a sheet conductor that is oriented roughly parallel with the local house field. An example is shown in FIG. 1, where a sheet conductor in the form of aluminum foils 43 is placed against the underside of a bed, and a continuation 43' of the foil covers the back of the headboard. The house field diminishing effect of a properly placed and oriented sheet conductor can be readily understood as due to electric polarization of the sheet conductor by the house field.

There is further concern about the effect of house field induced electric polarization of the electrode assembly, that may occur at times when no external electric field is being generated by the apparatus, but a connection exists between the field electrodes by virtue of the device circuit. This state occurs during most of the night, if the apparatus of FIGS. 3 or 4 is used as a sleeping aid with permanently placed field electrodes, after automatic shutoff has cut the power to the oscillator. Of concern is the circuit comprised of the two field electrodes, their connections to the generator, and pertinent output circuitry in the generator. Referring to FIG. 3, it is seen that this circuit includes the capacitor 22 and part of the potentiometer 12. The house field generally induces polarization currents in this circuit. The resulting polarization charges on the field electrodes induce an electric field with a nonuniformity scale comparable to the electrode spacing. This 60 Hz field may cause modulation of the same afferent nerves as those involved in the purposeful modulation. The inadvertent modulation may cause weak fm signals of 60 Hz frequency in receptive neural circuitry. The unwanted signals may be diminished by using the sheet conductor described above. Alternatively, or in addition, polarization of the electrode assembly by the house field may be preventing by breaking the electric connection between the field electrodes by means of a switch (44 in FIG. 3) in one of the output leads of the signal generator. The switch may be ganged with the power switch or controlled by the automatic shutoff circuit.

Figure 11:
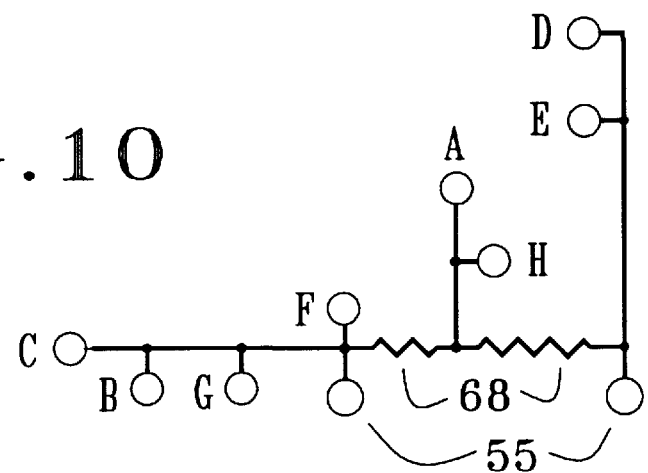
FIG. 11 shows the equivalent circuit for the subject exposed to an electric field as in the configuration of FIGS. 1 and 2.
Figure 11:
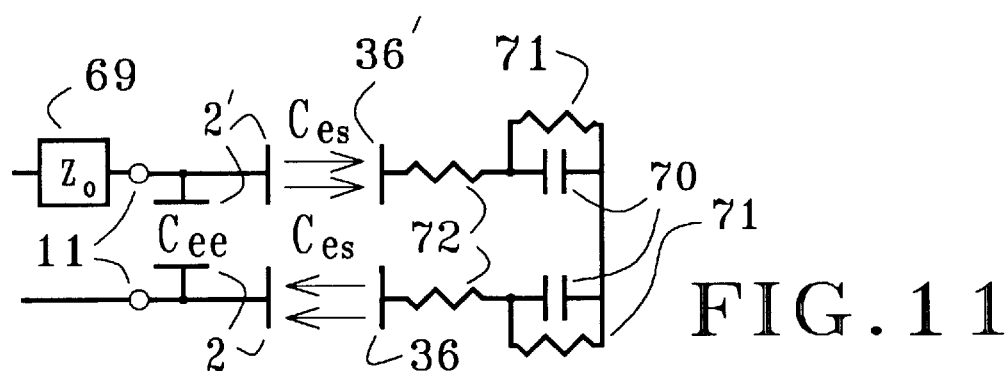

For proper design and application of the disclosed devices one needs to know the electric effects induced in an exposed subject. These effects can be calculated by considering the field application as a capacitive coupling of the field electrodes to the subject's body. FIG. 11 shows an equivalent circuit for the situation, where the output terminals 11 of the generator are connected to field electrodes 2 and 2', as in the configuration of FIG. 1. The external electric field induced by the field electrodes is predominantly applied to the skin areas 36 and 36', also shown in FIG. 2. The capacitance between field electrode 2 and the skin area 36 is denoted in FIG. 11 by $C_{es}$; the same capacitance is assumed between field electrode 2' and skin area 36'. The capacitance between the field electrodes by virtue of field lines that do not intersect the subject is denoted by $C_{ee}$. In FIG. 11, the portions of the electrodes that couple capacitively to the subject and the portions that couple to each other are shown as separate plates, for clarity of presentation. In the equivalent circuit the subject is modeled by series resistors R indicated by 72 and capacitors C (indicated by 70) that are shunted by resistors R indicated by 71. This lump-parameter circuit represents the electric properties of the bulk biological tissue involved, accounting for resistivity and permittivity. The impedance of the subject circuit is $$Z_s = 2\left(R' + \frac{R}{1+i2\pi f RC}\right), \quad (1)$$

where $i=\sqrt{-1}$, and f is the frequency of the voltage between the generator terminals 11. The imaginary term in (1) expresses the ratio of displacement current to conduction current in the subject's tissue. This ratio may be calculated from the bulk permittivity $\epsilon$ and the bulk resistivity $\eta$ of the tissue. The permittivity $\epsilon$ is very much larger than that of vacuum, owing to capacitive effects of the thin biological membranes. For very low frequencies Nunez gives $3.4\times10^6$ for the dielectric constant and $\eta=4.15$ Ωm for the resistivity, both for bulk muscle tissue. The norm of the imaginary term in (1) then comes to $$2\pi f RC = 7.9\times10^{-6} f. \quad (2)$$

For sensory resonance frequencies f in the range 0.1 to 45 Hz this term is negligible compared with unity, and the same is true for harmonics in the absence of steep fluctuations in the generator voltage. The subject impedance is then purely resistive, $$Z_s = 2(R'+R) = 2R_1, \quad (3)$$

in good approximation. The extended circuit that includes the capacitance $C_{es}$ between field electrodes has the impedance $$Z = 2\left(\frac{1}{i2\pi f C_{es}} + R_1\right). \quad (4)$$

For the voltage between the skin areas 36 and 36' of the subject one finds $$V_s = V_o Z_s/Z = \frac{i2\pi f R_1 C_{es}}{1+i2\pi f R_1 C_{es}} V_o, \quad (5)$$

where $V_o$ is the voltage between the generator output terminals 11. In order to estimate the imaginary term in (5) one writes $$R_1 = \eta l/A, \quad (6)$$

where A is the area of skin region 36 or 36', l is a significant depth of tissue, and $\eta$ is the resistivity of the bulk tissue. The capacitance $C_{es}$ may be written $$C_{es} = \epsilon_o A/d, \quad (7)$$

where $\epsilon_o$ is the permittivity of vacuum and d is a scale distance that characterizes the gap between field electrode and the subject's skin. In this manner one finds the estimate $$i2\pi f R_1 C_{es} = i2\pi f \epsilon_o \eta l/d. \quad (8)$$

For practical configurations the ratio l/d ranges about from 4 to 400. Using the value $\eta=4.15$ Ωm given by Nunez and $\epsilon_o=8.854$ pf/m, it is found that the magnitude of the term (8) is negligible compared with unity for sensory resonance frequencies and their harmonics, in the abstence of steep voltage fluctuations. Then the voltage between the skin areas 36 and 36' is negligible compared with $V_o$, so that the subject's skin may be considered an equipotential surface, for the purpose of external electric field calculations. The amplitude of the current density in the exposed skin area and the underlying tissue of the subject is then found to be $$j = 2\pi f \epsilon_o E_o, \quad (9)$$

if $V_o/(2d)$ is approximated by $E_o$, the external electric field standing on the skin. The same result is found from a one-dimensional model of a sinusoidal electric field applied perpendicular to a semi-infinite slab of uniform leaky polarizable material at frequencies for which the displacement current can be neglected. As mentioned in the Background Section, we consider polarization current densities in the brain substantial if the amplitude j of (9) exceeds 70 fA/cm$^2$.

The calculations are easily modified for the case that the capacitances between field electrodes and skin areas 36 and 36' differ from each other. For wave forms with steep transitions the tissue currents can be calculated from the model of FIG. 11, retaining terms negected above as the need arises. For some cases the generator output impedance $Z_o$ indicated by 69 and the capacitance $C_{es}$ may have to be accounted for. For the low frequencies involved, the skin effect does not affect the bulk paths of the polarization currents.

The polarization current (9) drives ions to the surface of the skin of an isolated subject, giving rise to a surface charge density $$q = \epsilon_o E_o, \qquad (10)$$

which follows of course also directly from the one-dimensional model mentioned, considering that the electric field in the tissue is negligible for pertinent cases.

Presently, the experiments that underlie the invention will be discussed. The experiment setup used initially was much like the one shown in FIG. 1, with variations as to the skin area of predominant field application. The voltage applied between the field electrodes was usually a rounded square wave with a frequency that can be manually tuned from 0.1 to 3 Hz, by adjusting the tuning control 21 on the generator 1 of FIG. 1. Frequencies at which a physiological effect occurs were found by manual frequency scanning. For the ½ Hz autonomic resonance, ptosis of the eyelids was used as an indication that the autonomic nervous system was affected. There are two ways in which this indicator may be used. In the first the subject simply relinguishes control over the eyelids, and makes no effort to correct for any drooping. The more sensitive second method requires the subject to first dose the eyes about half way. While holding this eyelid position, the subject rolls the eyes upward, while giving up voluntary control of the eyelids. With the eyeballs rolled up, ptosis will decrease the amount of light admitted into the eyes, and with full ptosis the light is completely shut off. The second method is very sensitive because the pressure excerted on the eyeballs by the partially closed eyelids increases parasympathetic activity. As a result the eyelid position becomes labile, as evidenced by a slight flutter. The labile state is sensitive to small shifts in sympathetic and parasympathetic activity. The method works best when the subject is lying flat on the back and is viewing a blank wall that is dimly to moderately lit.

With this arrangement maximum ptosis occurred at a frequency near ½ Hz, with external electric field amplitudes on the skin ranging from 1 to 25 V/m, where field amplitude is defined as half the peak-to-peak variation in the field strength. Immediately after onset, the ptosis frequency, defined as the frequency for maximum ptosis, slowly decreases until a steady frequency is reached in 5 to 10 minutes. This is thought to be due to changes in the chemical environment of the resonant neural circuitry, caused by changes in the concentration of neurotransmitters or homones that accompany or result from the resonance or from the subsequent change in the autonomic nervous state. The slow shift of ptosis frequency initially is so large that ptosis is lost if the frequency is not adjusted. The ptosis is accompanied by a state of deep relaxation, and a slight dull pressure at a spot about 1 cm above the bridge of the nose.

As directly demonstrated by the ptosis experiments, the present invention can be used for inducing relaxation in a subject. In further experiments with the device of FIG. 3 it has been found that, in the frequency range from 11% below to 4% above the ptosis frequency the subject became very relaxed after a few minutes of field application, using peak field strengths on the skin of about 1 V/m. Other autonomic responses can be obtained as well; tuning to 0.540 Hz brought on a tonic smile, provided that the subject gives up voluntary control of the facial muscles involved, so that the smile is controlled by the autonomic nervous system.

The method and apparatus can also be used for the induction of sleep. Tests running for about 400 nights were conducted on a subject who had trouble sleeping due to prolonged severe situational stress. In these tests, an external electric field was set up by applying a square wave voltage of 20 V peak to peak between two field electrodes placed directly beneath the bed sheet on both sides of the hips. Good results were obtained with frequencies of about ½ Hz. More recently, the device of FIG. 4 with a 3 V battery has been used for about 300 nights, under the same stressful conditions. Among the various electrode positions tried, the placement depicted in FIG. 1 was found to be most effective for inducing peaceful sleep. In this configuration the field electrodes 2 are located directly under the mattress, in the vertical symmetry plane through the long axis. The maximum electric field amplitude on the subject's skin is estimated as about 1 V/m. Two modes of operation were used. In the first mode, the unit was turned on at bedtime, at a frequency of 0.545 Hz. After 15 minutes, the device automatically shifts upward by 3%, and it turns off the oscillator after another 15 minutes. A second mode of operation involves initial tuning for ptosis, followed by manual tracking of the slowly downshifting ptosis frequency, using the tuning control 21 shown in FIG. 1. About 5 minutes after a steady ptosis frequency is reached, the device is shut off manually. Tracking the ptosis frequency during its downward shift brings an increasingly deep state of relaxation and detachment. Sleep usually follows shortly after the device is shut off manually.

At frequencies somewhat different from the ptosis frequency, sexual arousal has been observed. In a male subject 67 years of age the incidence of morning erections increased considerably when a rounded square wave voltage was applied to field electrodes 2 placed as shown in FIG. 1, at a frequency of 0.563 Hz, and also to a lesser extent, at 0.506 Hz. These frequencies were found by manual scanning in the range from 0.1 to 3 Hz. The signal generator of FIG. 3 was used, powered by a 3 V batttery. For frequencies near 0.550 Hz, rather intense sexual excitement lasting for up to an hour has been induced in a man 70 years of age, by applying the external electric field predominantly to a skin area that includes the perinaeun skin.

There needs to be concern about kindling of epileptic seizures in susceptable individuals. Kindling has traditionally involved passage of currents of the order of 0.1 mA directly to a part of the brain, such as the amygdala. Although in the present invention substantial polarization current densities in the brain are avoided, an effect similar to kindling might occur if critical neural circuits are subjected to repeated sessions of periodic fm signals from somatosensory or visceral afferents. To guard against such an effect, the frequency of modulation of afferents for use by the general public should be chosen away from frequencies involved in epileptic seizures. Modulation frequencies below 2 Hz may perhaps qualify in this regard.

The pathological oscillatory neural activity involved in epileptic seizures is influenced by the chemical milieu of the neural circuits that partake in the oscillation. Since the excitation of the sensory resonance may cause a shift in neurotransmitter and hormone concentrations, external electric fields may be useful for the control and perhaps treatment of seizures. For this purpose, the patient wears compact field electrodes and a voltage generator, to be manually activated when the patient experiences a seizure precursor or aura. A small box that contains the field electrodes as well as the generator may be suitable for this purpose.

The modulation of afferents by external electric fields may also be used for the control of tremors in Parkinson patients, by interfering with the underlying pathological oscillatory activity. Upsetting such activity by modulating afferent nerves by means of an external electric field tuned to a frequency slightly different from that of the pathological oscillation may also be useful for the control of seizures.

The method may be applied for the control of panic attacks, when these involve an abnormally high activity of the sympathetic nervous system. The experiments on ptosis, relaxation and sleep suggest that fluctuating external electric fields can diminish sympathetic activity. The apparatus of FIG. 3 may be used, tuned to a frequency just below ptosis, or, for severe cases, right at ptosis. In this application it is convenient to use a generator and field electrodes mounted in a single casing, such as a small box, wallet, purse, or the powder box of FIG. 6.

The manipulation of the nervous system by external electric fields tuned to a sensory resonance frequency is of course subject to habituation, sensitization, classical conditioning, and the placebo effect. To minimize habituation in the use as a sleeping aid, the field should be predominantly applied to a different skin area each night. Sensitization, the placebo effect, and positive classical conditioning enhance the efficacy of the method. Clinical trials can be designed such that the placebo effect does not contribute to the statistical mean. This is done by arranging the generator output to the field electrodes to be passed or blocked by computer, according to a pseudo-random sequence with a seed determined by date and time. Whether the field was on or off is unknown until the run is complete and the response of the subject has been entered into the computer. The arrangement is equivalent to a trully double-blind study.

In the configuration of the Brennan patent, the two field electrodes are positioned on opposite sides of the subject's head. This configuration restricts compactness and portability of the equipment as well as convenience of use.

In the present invention the field electrodes are placed on one side of the subject's body. For certain important cases this diminishes the practically obtainable field strength on the subject's skin, but application of the electric field to afferent nerves instead of directly to the brain and exploitation of sensory resonances makes it posssible to employ weak fields, thereby rendering the configuration broadly viable. The electrode configuration of the present invention allows the field application to be restricted to one or a few limited skin areas.

In the present invention the subject is entirely outside the space between the field electrodes. The space between two field electrodes is defined as consisting of all points P through which a straight line exists that intersects the two field electrodes at points that lie on opposite sides of P.

For the special case of field electrodes that form a parallel-plate condensor, the field outside the space between the field electrodes is commonly known as the fringe field. The same type of field with much the same utility is induced outside the space between any pair of field electrodes that are charged to opposite polarities; the electrodes need not have the same shape or size, nor do they need to be parallel or planar or directly apposed to each other. Since the electrodes are charged to opposite polarity, the pair of field electrodes may be seen to form a two-plate condensor. If the pair consists of two field electrodes that are roughly parallel and apposed to each other, it is here called a doublet, but it is not necessary that the field electrodes of a doublet have the same shape and size.

The type of field electrode configuration of the present invention is illustrated in FIG. 7, which shows a pair of field electrodes 2 and 2' connected by conductors 3 to an input port 55 that receives a fluctuating voltage from the generator 1, labeled "GENERATOR". The pair is positioned such that the subject 4 is entirely outside the space 46 between the field electrodes. Optionally, dielectric sheets 53 may be used for insulation.

Upon being charged to opposite polarity, the field electrodes of the pair induce outside the space 46 the electric field illustrated in FIG. 8. Shown are the field electrodes 2 and 2', the space 46 between the electrodes, the subject 4, and several field lines 5 impinging on the subject.

Figure 9:
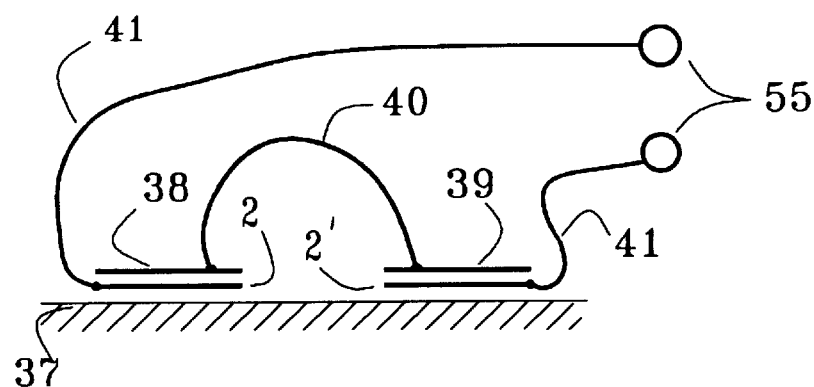
FIG. 9 shows two pairs of field electrodes, balanced for localized field administration.
Figure 10:
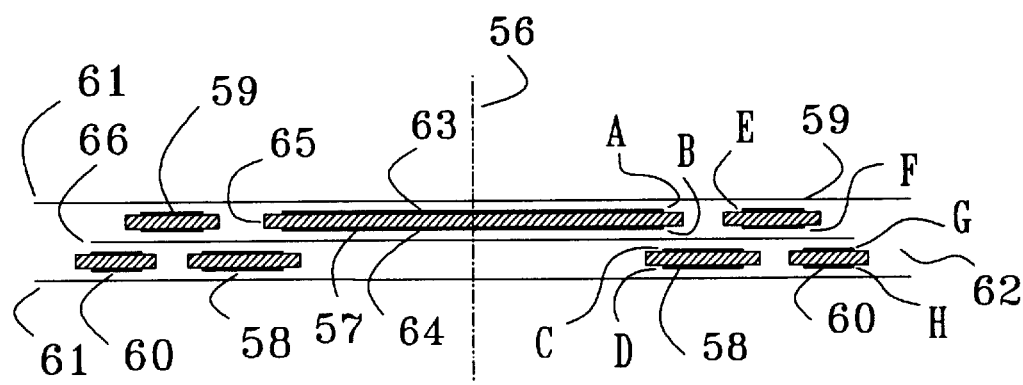
FIG. 10 depicts a multipole field electrode for producing a short range electric field.

In FIG. 7, the field electrodes are connected by conductors 3 to an input port 55 for receiving a fluctuating voltage. This connection is straightforward for the single electrode pair of FIG. 7, but for multiple pairs more complicated connections may be desired, and voltage dividers may be used as well. Such connections and voltage dividers are provided by a distributor which charges the electrodes of each pair to opposite polarity, upon receiving a fluctuating voltage at the input port. Examples for distributors for pairs of field electrodes are shown in FIGS. 9 and 10, to be discussed. The straigthforward set of connections 3 for the single electrode pair of FIG. 7 is seen as a special case of a distributor.

In certain experiments and clinical applications there is a need for an external electric field that is strictly confined to two selected skin regions. Such a field can be set up with two electrode pairs as depicted in FIG. 9, where field electrodes 2 and 2' are closely apposed, in parallel fashion, respectively by electrodes 38 and 39 called shield electrodes. A conductor 40 connects the shield electrodes, so that they have the same potential. Electrodes 2 and 2' are connected by wires 41 to the input port 55 which is to receive a voltage from the generator. Although not shown, insulation is applied between electrodes 2 and 38, and between electrodes 2' and 39. Optionally, insulation is applied to the top and bottom of the two resulting structures as well, so that two five-layer sandwiches result. The two field electrode pairs are placed in close proximity of the skin 37 of the subject, in the orientation shown in FIG. 9. The voltage between the shield electrodes and the skin is determined by two capacitive voltage dividers. This voltage is zero if the ratio of the capacitance between electrodes 2 and 38 and the capacitance between electrodes 2' and 39 is the same as the ratio of the capacitance between electrode 2 and the skin 37 and the capacitance between electrode 2' and the skin 37. In that case, no field lines stand between the shield electrodes and the subject's skin, and we will say that the two electrode pairs are balanced. The external electric field is then confined to four narrow spaces, viz., the space between electrode 2 and the skin 37, between electrode 2' and the skin, between electrode 2 and the shield electrodes 38, and between electrode 2 and shield electrode 39, except for edge fields pouring from the edges of the narrow spaces. These edge fields extend over a distance of the order of the electrode separation or the distance from electrode 2 or 2' to the skin. If these separations are very small, so will be the spatial extents of the edge fields, and the external field on the skin will then be essentially confined to the skin areas directly apposed by the electrodes 2 and 2'. Electrodes 2 and 2' need not be positioned in close proximity to each other. The conductor 40 may be a conductive foil, which may simply be the continuation of the shield electrodes 38 and 39.

The balanced electrode pairs of FIG. 9 can be seen as two pairs of field electrodes that are connected in series, and therefore as a special case of pairs of field electrodes with a distributor. In this case the distributor comprises the connections 41 between the field electrodes and the input port 55, as well as the connection 40 between the shield electrodes 38 and 39. Balancing may be applied to more than two field electrode pairs, in order to restrict the field application to more than two skin areas.

The balanced pairs may be doublets. A pair of field electrodes may be used in the compact configuration wherein the field electrodes are contained together with the generator in a single casing, such as the powder box of FIG. 6. The electrode configuration of FIG. 1 is a special case of a pair of field electrodes charged to opposite polarity and placed such that the subject is entirely outside the space between the field electrodes.

There sometimes is a need for a short range electric field that is produced by field electrodes placed some distance away from the subject's body. This can be accomplished with an assembly of field electrode pairs designed such that their combined field is asymptotically multipole, i.e., at large distances r, the potential falls off as $1/r^k$, with k>2. The integer k is called the order of the multipole. An assembly of field electrode pairs with this property is here called a multipole field electrode. In order to see how to build such an electrode, consider that in free space the potential for the field induced by an axisymmetric assembly of m field electrode pairs has a so-called multipole expansion with terms of the order of $1/r^2$, $1/r^4$, $1/r^6$, etc. Each of these terms is the sum of contributions from the individual field electrode pairs. It is possible to choose the geometry and driving voltages of the electrode pairs such that for each of the first m−1 terms in the multipole expansion the individual contributions cancel each other. The m electrode pairs are then said to be fully compensated. The leading term of the multipole expansion is then of the order $1/r^{2m}$, so that the field produced by the assembly is asymptotically multipole of order 2m.

A practical multipole electrode can be designed as follows. Consider, in a plane, an assembly of m concentric circular field electrode pairs each of which forms a parallel-plate condenser, with radii $R_j$, and voltages $V_j$, j=1 to m. It can be readily shown that the first m−1 terms in the multipole expansion of the electric potential induced by the assembly vanish, i.e., the assembly is fully compensated, if $$\Sigma R_j^2 V_j=0, \ \Sigma R_j^4 V_j=0, \ldots \Sigma R_j^{2m-2} V_j=0, \tag{11}$$

with the sums taken over j=1 to m. This is a Van der Monde system that can be solved, for any m, by a modification of the Pascal triangle for the binomial coefficients. The modification entails starting each row of the triangle with the row number, and completing the row by the well-known Pascal triangle construction. One thus finds for the first row 1, for the second row 2,1, for the third row 3,3,1, for the fourth row 4,6,4,1, etc. For the assembly of m doublets, the modified Pascal triangle must be completed up to row m. The voltages $V_j$ are then to be taken proportional to the sequence of numbers in the mth row of the triangle, with alternating signs. The squared radii, $R_j^2$, of the individual doublet discs are to be taken proportional to the index j. The resulting $V_j$ and $R_j$ satisfy Eq. (11), as can be verified by substitution. The superposition of m electrode pairs can be implemented in practice by adding the voltages in the regions of overlap, and applying these sums as driving voltages to annular electrode pairs with radii $R_{j-1}$ and $R_j$, $R_0$ being chosen as zero. As an example for m=4, one has a central electrode pair of radius R driven by a voltage V, an annular electrode pair with inner radius R and outer radius R√2 driven by the voltage −3 V, an annular electrode pair with inner radius R√2 and outer radius R√3 driven by a voltage 3 V, and an annular electrode pair with inner radius R√3 and outer radius 2R driven by the voltage −V. In practice the voltages are derived from an accurate resistive divider. The above calculations give a good approximation if the electrode separations in the individual pairs are very small, so that the areas of the electrodes that have considerable nonuniformities in charge distribution are negligible.

If the order of the multipole field electrode is increased, the asymptotic multipole field falls off faster, and a larger driving voltage is required in order to induce the same field strength at any fixed point far on the symmetry axis. Furthermore, finer fabrication tolerances are required, because the multipole action is based on full compensation, i.e., the cancellation of the lower order pole contributions. The latter two effects place a practical upper limit on the order of the multipole field electrode.

The field of a charged electrode pair polarizes adjacent electrode pairs. This cross coupling is unwanted, since it complicates design of the multipole field electrode. The coupling can be kept to negligible levels by choosing the two field electrodes of each pair to be very close to each other.

The cancellation of the lower order terms in the multipole expansion occurs in the asymptotic field, i.e., in practice at distances large compared to the size of the multipole. At such distances however, the field is very weak, owing to the rapid falloff of the multipole field, together with practical limitations on the generator voltage. Hence, at useful distances, the field may have significant components that deviate from the leading multipole term. These terms may need to be calculated in order to estimate the strength and pattern of the field applied to the subject's skin. At large distances the asymptotic multipole field behavior takes hold, and the range restriction is thereby accomplished.

The structure of the multipole electrode of order 8 of the type discussed above is shown in FIG. 10 as an axisymmetric assembly of individual electrode pairs 57, 58, 59, and 60 with symmetry axis 56. Each of these electrode pairs forms a parallel plate condensor. The electrode pair 57 has the shape of a disc, whereas the electrode pairs 58, 59, and 60 have annular shape. The assembly of electrode pairs is fastened to two adhesive sheets of insulation 61, which are stuck together in the border region 62. An insulating layer 66 is applied between the upper assembly consisting of the electrode pairs 57 and 59, and the lower assembly consisting of the electrode pairs 58 and 60. Each of the pairs consists of two field electrodes, such as 63 and 64 for the pair 57, insulated by a dielectric layer 65. Here, the distributor involves a resistive voltage divider 68 and connections to the various points in the electrode pair assembly and to the input port 55 that is to receive a fluctuating voltage. For readability of the drawing, some of these connections are implicitly indicated as pairs of identical letters placed at certain connection points; such point pairs are understood to be electrically connected.

The multipole electrode of FIG. 10 has four electrode pairs which together cover a geometric disc without leaving gaps. However, configurations with gaps can be designed, by considering each gap as an annular electrode pair with zero driving voltage. The coefficients $R_j^2$, $R_j^4$, etc. in Eq. (11) are then replaced by differences of powers of the outer and inner radii of the annular gaps, as will be evident by carrying out the multipole expansion of the electric potential. The solution by the modified Pascal triangle no longer holds, but the equations that express full compensation, i.e., the vanishing of the first m−1 terms in the multipole expansion, can be readily solved numerically. Non-axisymmetric multipole electrodes can be designed as well, but the analysis then requires spherical harmonics; full compensation is again defined in terms of the asymptotic potential, as the optimal cancellation of lower-order terms.

A multipole field electrode of order 8 has been built as a circular planar sheet, with a central electrode pair of R=6.25 cm radius. The multipole electrode induces an electric field with a lobe structure, so that on the subject's skin there is a set of zones of positive and negative field amplitudes. The setup with the multipole field electrode placed under the mattress at lumbar level has been tested as a sleeping aid for about 30 nights, with good results. With the same setup, a man 70 years of age can experience rather intense sexual excitement lasting for about an hour, by assuming a position on the mattress such that the central emission lobe from the multipole electrode intersects his perinaeum.

Fixing all experiment parameters except for the field strength, the described physiological effects are observed only for field intensities in a limited interval, here called "the effective intensity window". This feature of sensory resonance may be understood as due to nuisance-guarding neural circuitry that blocks impertinent repetitive sensory signals from higher processing. For the guard circuitry to spring into action, the nuisance signal needs to exceed a certain irritation threshold. This explains the existence of the upper boundary of the effective intensity window. The lower boundary is due to the fm detection threshold of processing circuits.

It has been observed that, for larger exposed skin areas, lower field strengths suffice for the excitation of sensory resonances. This "bulk effect" is important for the proper use of the invention, and can be understood as due to an increase of the signal to noise ratio of the fm in the output of summing neurons, when the number of frequency modulated afferents is increased. For affected cutaneous receptors with uniform surface density $\rho$ one expects the observable response of application to the skin area $A_s$ of an external field with amplitude $E_o$ and frequency f to be a function of $E_o\sqrt{(f\rho A_s)}$, as can be shown assuming that the unmodulated spontaneous spiking of the afferents produces in the dendrite of a summing neuron a Poisson stream of charge injections. For fixed f and $\rho$ it seems therefore best to express the effective intensity window in terms of $E_o\sqrt{A_s}$. Experiments for exploring the window for the 2.4 Hz sensory resonance have been conducted using as field generator a parallel plate condensor type pair of field electrodes driven by a sine wave of 1.25 V amplitude and a frequency near 2.4 Hz. The electrode pair was placed at distances from the subject ranging from 64.5 to 208 cm, about at hip height. At these distances a large skin area is exposed to the field. For each distance the maximum field induced on the subject's skin was estimated, using the method of images to account for polarization charges induced on the subject's skin. In terms of the parameter $E_o\sqrt{A_s}$, the effective intensity window was found to extend from 17 to 123 mV. The window of course depends on the surface density of the cutaneous receptors that are modulated by the field.

In the experiment discussed above different field strengths on the subject were obtained by placing the electrode pair at different distances. Another experiment was performed in which the skin area $A_s$ was fixed, and the field strength was varied by changing the voltage applied to the field electrodes. The latter were two balanced pairs with field electrodes of 223×230 mm applied to the thighs of the subject a distance of 5 mm from the skin. A sinusoidal voltage was applied to the electrodes, with frequency of 2.408 Hz and an amplitude of 1.25 V. The skin area $A_s$ is here the same as the electrode area of 513 cm². In terms of $E_o\sqrt{A_s}$, the effective intensity window was found to extend from 18.2 to 158 mV. Considering differences in the surface density of pertinent cutaneous receptors for the two experiments described, the measured windows are consistent with the notion that the physiological response to the external field application is a function of the parameter $E_o\sqrt{(f\rho A_s)}$.

One sometimes needs to reduce data on effective intensity windows such as to eliminate the effect of the surface density $\rho$ of cutaneous receptors that are affected by the field. A convenient parameter of this type is the span of the window, defined as the ratio of the upper to lower boundary of the window.

The mechanism of the human electroception discovered and discussed here is unknown. For the experiments performed, the polarization current (9) always is orders of magnitude too small to cause quiescent nerves to fire. However, as pointed out by Terzuolo and Bullock, modulation of the frequency of an already active neuron can be achieved with voltages very much lower than those needed for excitation of a quiet neuron. Voltage gradients as small as 1 V/m across the soma were sufficient to cause a marked change of firing of adaptive stretch receptors of crayfish. Terzuolo and Bullock further remark that the value of the critical voltage gradient for this effect may actually be much smaller than 1 V/m. Unfortunately, in our weak field experiments the polarization current density j of (9) and the accompanying internal electric field appear too small to cause even this effect. However, thermal motion of ions cause smearing of the surface polarization charge density (10) over a layer with thickness of the order of the Debye length, so that the applied external field penetrates to some depth into the skin instead of ending abruptly at the outer skin surface. Cutaneous receptors present at that depth will be exposed to an electric field with a strength of the order of the applied external field. This electric field may perhaps be strong enough to modulate the spontaneous spiking of slowly adapting mechanoreceptors such as Ruffini endings and Merkel cells, which are found roughly at a depth of 0.2 mm in the skin.

Thus far arrangements have been discussed where the modulation of afferents by the field occurs in cutaneous receptors. An essentially different situation of interest occurs when the tissue underlying the skin area of predominant field application is traversed by a nerve that has no receptors in the overlying skin. The question then arises whether the spike trains carried by the afferent fibers in the nerve can be modulated without causing classical nerve stimulation. Since polarization charges on the skin cannot have an effect in this case, any modulation occurring must be due to currents. Since the origin of the currents does not matter, they may as well be introduced by contact electrodes, thereby affording simple control of the current magnitude for research purposes. An experiment was done in which currents in the tissue were produced by two contact electrodes (3M red dot$^{Ym}$, 22×22 mm) placed on the skin at the back of the right knee, with a center-to-center separation of 45 mm, such as to expose the underlying sciatic nerve to longitudinal currents. For a sinusoidal current with a peak density amplitude of 3.4 nA/cm$^2$ at a frequency of 2.410 Hz, the 100–60 counts showed excitation of the 2.4 Hz resonance. The current density of 3.4 nA/cm$^2$ is much too small for causing classical nerve stimulation. No excitation was found for a similar current injection transverse to the nerve. The experiments show that indeed, afferent fibers in a nerve can be modulated by artificial electric currents without undergoing classical nerve stimulation. The finding that transverse currents do not excite the resonance shows that the modulation is really done on the afferent fibers, and not on receptors. Similar results were found for sinusoidal current applications to the skin over the right vagus nerve in the neck. Exposure to longitudinal currents in the range from 200 pA/cm$^2$ to 60 nA/cm$^2$ caused excitation of the 2.4 Hz resonance, but transverse currents showed no effect.

In both these experiments it appears that longitudinal artificial currents in the tissue surrounding the afferent can affect the propagation velocity of action potentials in the nerve; pulsing the applied currents would then result in frequency modulation of the spike trains received by the brain. Since the propagation velocity of action potentials along an axon is influenced by the membrane conductance, and the latter is a sensitive function of the membrane potential, it is plausible that the propagation speed can be modulated by perturbations of the membrane potential that are brought about by longitudinal currents superimposed on the currents that accompany the action potential propagation, considering the nonuniformities of conductivity in the current path distribution. These propagation speed modulations, small as they are, may perhaps evoke an fm signal in the brain that suffices for the excitation of a sensory resonance. The influencing of the action potential propagation speed along an axon by an external electric field is of great importance to neural science and needs to be investigated further.

Excitation of the ½ Hz resonance is possible with large external electric fields, up to 10 KV/m, produced by placing an insulated pair of field electrodes directly on the skin of the thighs. A sweat layer then quickly develops between the skin and the mylar sheet that covers the field electrode. This highly conductive sweat layer removes the polarization charges from the skin so that the mechanism of Debye smearing of the polarization charges in the skin cannot operate. Therefore, the modulation of cutaneous nerves in this case must be due to polarization currents. For the rounded square wave used, the peak polarization current density in the skin apposing the field electrodes is found to have an amplitude of about 100 nA/cm$^2$. Since the afferents of the cutaneous nerves in the dermis are oriented roughly perpendicular to the skin surface, the local polarization current is longitudinal with respect to the afferent fibers, so that one expects the afferents to be subject to modulation by the currents, at least by virtue of the action potential propagation speed effect discussed. In addition, the cutaneous receptors may respond as well to the large polarization currents. The modulation of cutaneous nerves by the large external field of 10 KV/m in the presence of a sweat layer between skin and field electrode insulation is thereby understood to about the same extent as the other modulation situations. It is emphasised that the polarization current density of 100 nA/cm$^2$ is still much too small to cause classical nerve stimulation.

Strong fields applied to areas of skin overlying nerves may be used for modulating afferent fibers in these nerves, thereby providing a method for manipulation of the nervous system via visceral afferents, as in the vagus nerve. The method differs from that of Wernicke et al. and from that of Terry et al., in that it employs field electrodes rather than contact electrodes, so that it is noninvasive, and there is no reliance on classical nerve stimulation, so that current densitites smaller by a factor 50000 suffice. Furthermore, the present invention uses excitation of sensory resonance. In our experiments, two balanced pairs of insulated field electrodes are placed on or adjacent to the skin such that the line connecting their centers is roughly parallel to the underlying nerve, afferents of which are to be modulated. The field strength needed for the excitation of sensory resonances can be calculated from (9) if the necessary current densities are known. For the excitation of the 2.4 Hz resonance through the vagus nerve, the effective intensity window in terms of current density is found to extend from 21 pA/cm$^2$ to 41 nA/cm$^2$. Using (9), the corresponding field strengths for a sine wave are found to range from 3.8 KV/m to 7.6 MV/m. A low voltage sine wave generator suffices for the production of fields in a low part of this range, if the two balanced pairs of insulated field electrodes are placed directly on the skin. For instance, with insulating tape 0.076 mm thick (3M Scotch$^{Ym}$ Mailing Tape), a voltage amplitude of 1 V gives a field of 13.2 KV/m.

Strong-field experiments have been conducted on the sciatic nerve underlying the skin on the back of the knee, using an insulated doublet with 60×42 mm area. With the doublet positioned in the skin fold of the bent knee, and an 162×135 mm insulation sheet provided such that the polarization currents cannot be shortened by apposing skin of calf and thigh, the sciatic nerve was exposed to longitudinal polarization currents of the order of 50 pA/cm$^2$, caused by fields of about 3.7 KV/m set up by a sine wave voltage of 1.13 V amplitude at a frequency of 2.414 Hz. Silent counting from 100 to 60 showed that the 2.4 Hz resonance was excited.

A similar experiment was done in the right armpit, exposing the ulnar nerve to longitudinal polarization currents that were caused by a 60×42 mm field electrode pair inbedded in the 162×135 mm insulation sheet discussed above, using the same voltage amplitude and frequency as before. The 100–60 counting showed excitation of the 2.4 Hz resonance.

Finally, a strong-field experiment was done on the right vagus nerve in the neck, using two balanced doublets of 22×22 mm area, at a center-to-center distance of 45 mm, oriented such as to expose the nerve to longitudinal polarization currents. The field electrodes were driven by a sinusoidal voltage with an amplitude of 1.13 V and a frequency of 2.414 Hz. Again, the 100–60 counting showed excitation of the 2.4 Hz resonance. In spite of the rather close proximity of the skin area of predominant field application, the brain was not subjected to substantial polarization current densities, by virtue of the strict field localization by the balanced field electrode pairs.

The experiments discussed show that there are two mechanismss of modulation of afferents by an electric field applied to the skin. The first mechanism, called charge modulation, involves modulation of cutaneous sensory receptors by the weakened external field as it penetrates a short distance into the skin due to the thermal smearing of polarization charges. In the second mechanism, called current modulation, the polarization currents are strong enough to cause modulation of the propagation speed of action potentials along axons exposed to the currents. It appears that both mechanisms are possible even when the polarization currents are much too weak to cause classical nerve stimulation. Sensory resonances can be excited with both these mechanisms, but the effective intensity windows have different spans. For the 2.4 Hz sensory resonance the window for charge modulation mechanism extends roughly from 20 mV to 140 mV in the parameter $E_{max}/A_s$, to be adjusted for different densities of the affected cutaneous receptors. With current modulation, the effective intensity window extends roughly from 21 pA/cm² to 41 nA/cm², to be adjusted for the number of affected afferents in the nerve exposed to the polarization currents. The span of about 2000 for this window compared to about 8 for charge modulation shows that different mechanisms are involved. Current modulation is suitable for manipulation of the nervous system through visceral or somatosensory afferents in large nerves that are, at places, capacitively accessible through the skin, such as vagus and sciatic nerves. In these cases, the application of external fields can be done with two balanced pairs of field electrodes, placed on the overlying skin in the direction of the nerve. When used properly, the balanced electrode pair assures that the field is applied strictly to the underlying skin, without exposing more distant regions of the body, such as the brain, to substantial polarization currents. The field strengths appropriate for exitation of sensory resonances through the two mechanisms differ by a large factor; for charge modulation, typical fields on large skin areas range from 10 to 200 mV/m, whereas for the current modulation the fields, naturally for localized small skin area exposure, are of the order of kilovolts per meter. For both mechanisms, the proper fields can be produced by the same low voltage generator, simply by using different field electrodes and deployment. A field electrode pair placed some distance from the subject is particularly suitable for charge modulation of cutaneous receptors over large skin areas, whereas the two balanced pairs is the field electrode configuration of choice in the current modulation regime.

The method is expected to be effective also on certain animals, and applications to animal control are therefore envisioned. The nervous system of humans is similar to that of other mammals, so that sensory resonances are expected to exist in the latter, albeit with somewhat different frequencies. Accordingly, in the present invention, subjects generally are mammals.

The invention is not limited by the embodiments shown in the drawings and described in the specification, which are given by way of example and not of limitation, but only in accordance with the scope of the appended claims.

I claim:

1. Electric field generator for manipulating the nervous system of a subject, which comprises:

generator means for generating a fluctuating voltage;

at least one pair of field electrodes;

distributor means, responsive to the fluctuating voltage, for charging the field electrodes to opposite polarity;

said at least one pair of field electrodes to be positioned and oriented such as to render the subject entirely outside the space between the field electrodes.

2. The electric field generator of claim 1, further including a dielectric positioned between the field electrodes.

3. The electric field generator of claim 1, further including casing means for containing the generator means, the distributor means, and the at least one pair of field electrodes.

4. Electrode for use in an electric field generator for manipulating the nervous system of a subject, comprising:

an input port;

at least one pair of field electrodes;

distributor means, connected to the input port, for charging the field electrodes to opposite polarity when the input port is energized;

said at least one pair of field electrodes to be positioned and oriented such as to render the subject entirely outside the space between the field electrodes.

5. The electrode of claim 4, further including a dielectric positioned between the field electrodes.

6. A method for manipulating the nervous system of a subject, comprising the steps of:

generating a fluctuating voltage;

constructing a pair of field electrodes;

applying the fluctuating voltage between the field electrodes to induce an electric field; and placing and orienting said pair of field electrodes such as to expose the subject solely to the electric field outside the space between the field electrodes.

7. The method of claim 6 for exciting in the subject a sensory resonance, the sensory resonance having a resonance frequency, and wherein the fluctuating voltage has a frequency, the method further including the step of setting the voltage frequency to the resonance frequency.

8. A method for manipulating the nervous system of a subject, comprising the steps of:

selecting on the subject a skin area away from the head;

generating a fluctuating voltage;

constructing a pair of field electrodes;

applying the fluctuating voltage between the field electrodes to induce an electric field;

administering the electric field predominantly to said skin area, for modulating afferent nerves without causing classical nerve stimulation, and without causing substantial polarization current densities in the brain of the subject.

9. The method of claim 8 for exciting in the subject a sensory resonance, the sensory resonance having a resonance frequency, and wherein the fluctuating voltage has a frequency, the method further including the step of setting the voltage frequency to the resonance frequency.

* * * * *